US012778742B2

(12) United States Patent
Egnelöv

(10) Patent No.: US 12,778,742 B2
(45) Date of Patent: Nov. 3, 2026

(54) MESH SUPPORT DEVICE FOR A BREAST IMPLANT

(71) Applicant: NOVUS SCIENTIFIC AB, Uppsala (SE)

(72) Inventor: Wasana Egnelöv, Uppsala (SE)

(73) Assignee: NOVUS SCIENTIFIC AB, Uppsala (SE)

( * ) Notice: Subject to any disclaimer, the term of this patent is extended or adjusted under 35 U.S.C. 154(b) by 974 days.

(21) Appl. No.: 17/765,560

(22) PCT Filed: Sep. 28, 2020

(86) PCT No.: PCT/EP2020/077027
§ 371 (c)(1),
(2) Date: Mar. 31, 2022

(87) PCT Pub. No.: WO2021/063851
PCT Pub. Date: Apr. 8, 2021

(65) Prior Publication Data
US 2022/0362006 A1 Nov. 17, 2022

(30) Foreign Application Priority Data
Oct. 3, 2019 (SE) .................................... 1951127-8

(51) Int. Cl.
*A61F 2/12* (2006.01)
*A61F 2/00* (2006.01)

(52) U.S. Cl.
CPC .............. *A61F 2/12* (2013.01); *A61F 2/0063* (2013.01); *A61F 2210/0004* (2013.01);
(Continued)

(58) Field of Classification Search
CPC .. A61F 2/12; A61F 2220/0033; A61F 2/0063; A61F 2250/003
See application file for complete search history.

(56) References Cited

U.S. PATENT DOCUMENTS 6,015,428 A 1/2000 Pagedas
7,875,074 B2 1/2011 Chen et al.
(Continued)

FOREIGN PATENT DOCUMENTS

EP 2 002 800 A1 12/2008
EP 3 085 337 A1 10/2016
(Continued)

OTHER PUBLICATIONS

Swedish Search Report, Application No. 1951127-8, Apr. 1, 2020, 2 pages.
(Continued)

*Primary Examiner* — Thomas C Barrett
*Assistant Examiner* — Teresa M Dudden
(74) *Attorney, Agent, or Firm* — Foley & Lardner LLP

(57) ABSTRACT

The invention relates to a mesh support device (10) for supporting a breast implant, which mesh support device (10) comprises a first mesh panel (11), which comprises a first arm (31) having a length $L_1$ and a second arm (32) having a length $L_2$, and a second mesh panel (12), which comprises a first opening (21), which is arranged to receive the first arm (31), and a second opening (22), which is arranged to receive the second arm (32), wherein 30 mm<$L_1$<210 mm and 30 mm $L_2$<210<mm.

20 Claims, 5 Drawing Sheets

(52) U.S. Cl.
CPC . *A61F 2220/0033* (2013.01); *A61F 2250/003* (2013.01); *A61F 2250/0037* (2013.01)

(56) References Cited

U.S. PATENT DOCUMENTS

| | | | | |
|---|---|---|---|---|
| 8,016,841 | B2 | 9/2011 | Magnusson et al. | |
| 8,083,755 | B2 | 12/2011 | Mathisen et al. | |
| 9,566,370 | B2 | 2/2017 | Mathisen et al. | |
| 9,782,245 | B2 | 10/2017 | Mujwid et al. | |
| 2006/0142786 | A1* | 6/2006 | Mathisen | A61L 31/129 606/151 |
| 2008/0021265 | A1 | 1/2008 | Garbin et al. | |
| 2008/0161837 | A1* | 7/2008 | Toso | A61F 2/0045 606/151 |
| 2009/0082864 | A1 | 3/2009 | Chen et al. | |
| 2009/0318752 | A1 | 12/2009 | Evans et al. | |
| 2010/0023029 | A1 | 1/2010 | Young | |
| 2010/0234679 | A1* | 9/2010 | Evans | A61F 2/0045 600/37 |
| 2012/0185041 | A1 | 7/2012 | Mortarino et al. | |
| 2013/0304098 | A1 | 11/2013 | Mortarino | |
| 2014/0088344 | A1* | 3/2014 | Mujwid | A61F 2/0045 600/30 |
| 2016/0331504 | A1* | 11/2016 | Wang | A61B 90/02 |
| 2020/0222177 | A1 | 7/2020 | Paydar et al. | |
| 2020/0345476 | A1* | 11/2020 | Wang | A61L 27/362 |

FOREIGN PATENT DOCUMENTS

| | | | |
|---|---|---|---|
| WO | WO 2008/042434 | A2 | 4/2008 |
| WO | WO 2009/017680 | A2 | 2/2009 |
| WO | WO 2014/149096 | A1 | 9/2014 |
| WO | WO 2016/144885 | A1 | 9/2016 |

OTHER PUBLICATIONS

Non-Final Office Action on U.S. Appl. No. 17/764,820 mailed Nov. 6, 2024.

Swedish Search Report, Application No. 1951126-0, Mar. 30, 2020.

Final Office Action issued in U.S. Appl. No. 17/764,820 mailed Mar. 28, 2025.

Non-Final Office Action on U.S. Appl. No. 17/764,820 mailed Aug. 14, 2025.

Final Office Action in U.S. Appl. No. 17/764,820 dated Dec. 22, 2025.

* cited by examiner

MESH SUPPORT DEVICE FOR A BREAST IMPLANT

FIELD OF THE INVENTION

The present invention relates generally to a medical support device for supporting a medical implant and relates particularly to a mesh support device for supporting a breast implant, wherein the mesh support device comprises a first panel, a second panel, and at least two arms arranged at the first panel, which arms are relatively long and are configured to be inserted into corresponding openings provided in the second panel.

BACKGROUND OF THE INVENTION

A medical breast reconstruction is a medical procedure that typically involves the use of prosthetic breast implants, e.g. silicone or saline implants, which, during the medical procedure, are positioned either inside or outside the breast muscle, to recreate a female breast. Within the art of reconstructive and cosmetic breast surgery, it is further common to combine the breast implant with a support device, which is arranged to at least partly enclose the breast implant. The support device can then be attached, e.g. stitched, to the human breast tissue to thereby fixate the position of the breast implant, or the support device can simply provide a structure for facilitating and promoting tissue integration of the breast implant.

Support devices for breast implants are available in many types and designs but are typically made from a mesh material and have a flat back wall and a concave front wall. The mesh material used can be a permanent mesh material or can be made from a biodegradable material. Support devices of this type are, for example, disclosed in the U.S. Pat. No. 7,875,074 to Chen et al., wherein the support devices comprise a concave receiving space, which is defined by a back wall and a front wall for at least partly receiving and supporting a breast implant therein.

A common feature of the known support devices for breast implants is that they provide a pocket in which the breast implant is to be placed. However, breast implants come in several sizes and also shapes, which means that several support devices having pockets with corresponding sizes and shapes must be kept in store, which in itself poses a logistical problem, not least since a support device, which often is made from a bio-degradable material, typically has an expiry date that must not be exceeded.

In the published U.S. Patent Application No. 2013/0304098 to Mortarino, which relates to a three-dimensional fabric structure in the form of a pocket in which a breast implant is to be placed, it is in one embodiment described how the three-dimensional fabric structure can be created by means of a first mesh panel, which comprises a number of small tabs that are arranged to be inserted into corresponding slots in a second mesh panel, whereupon the tabs are sutured to the second mesh panel. The first and second mesh panels are, by a doctor or surgeon, created by imposing corresponding templates, having sizes proportional to the breast implant to be supported, over the mesh panels, and then trim to the mesh panels to the sizes and shapes of the templates.

Further, even if the size and shape of particular support device are well fitted to a specific breast implant, there is—typically due to the pocket-like shape—always a certain mismatch between the round or more or less hemi-spherically shaped breast implant and the outer rim area of the receiving pocket, i.e. the breast implant does not completely fill out the space where a back wall of the support device meets the front wall, which makes it difficult to exactly position the breast implant. Furthermore, many existing support devices for breast implants are by doctors and surgeons perceived to have a design that is too elaborated to be optimal from a medical perspective, i.e. the support devices require extra attention and special handling before and/or during the implantation procedure. Needless to say, any medical device which has a design that is not optimal from a medical perspective implies a certain risk for the patient.

Although a support device according to the prior art may serve its intended purpose well, it is still accompanied by problems related to its adaption to the size and shape of the breast implant that is to be supported by the support device in question. The known support devices are typically also associated with disadvantages when it comes to user-friendliness, i.e. how easy they are to handle by doctors and surgeons before or during an implantation procedure. A general object of the present invention is therefore to provide an improved support device for a breast implant, which support device has a design and shape that adapt to the size and shape of the breast implant and which can be easily adapted to a span of different implant sizes and shapes. Another object of the invention is to provide an improved support device which is easy to handle during a medical implantation procedure. A further object of the invention is to provide a mesh support device having a design that is easy to manufacture.

SUMMARY OF THE INVENTION

The above-mentioned objects are achieved by the present invention according to the independent claims. Preferred embodiments are set forth in the dependent claims.

Embodiments of the present invention relate to a mesh support device for supporting a breast implant, which mesh support device comprises a first mesh panel, which has a largest width $W_1$ and comprises a first arm, which has a length $L_1$ and is arranged at a first side of the first mesh panel, and a second arm, which has a length $L_2$ and is arranged at a second side of the first mesh panel, the second side being opposite to the first side, and comprises further a second mesh panel, which has a largest width $W_2$ and comprises a first opening, which is arranged or configured to receive the first arm, and a second opening, which is arranged or configured to receive the second arm. To provide for a support device which is easy to handle and which can accommodate breast implants having different shapes and sizes, it is, according to the invention, important that the first and second arms are relatively long and should, at the same time, not be excessively long, and it is therefore preferred that the lengths $L_1$ and $L_2$ are arranged such that 30 mm$\leq L_1 \leq$210 mm, and more preferably 70 mm$\leq L_1 \leq$180 mm, and most preferably 110 mm$\leq L_1 \leq$150 mm; and 30 mm$\leq L_2 \leq$210 mm, and more preferably 70 mm$\leq L_2 \leq$180 mm, and most preferably 110 mm$\leq L_2 \leq$150 mm.

The first mesh panel and the second mesh panel are configured to lay or be arranged opposite to each other when assembled to encapsulate a breast implant; and by inserting each of the arms of the first mesh panel into a respective opening provided in the second, opposite mesh panel, a space is created in which a breast implant is placed. With the breast implant in place between the first and second mesh panels, the arms are tightened, i.e. the arms are pulled such that a larger portion of the respective length of the arm has passed through the opening, and the breast implant is thereby firmly held in place between the first and second mesh panels. The arms and the corresponding openings have dimensions such that a friction locking is created between the inner contour of the opening and the arm inserted therein, which prevents that the arm slides back and out of the opening. That is, the mesh support comprises a number of openings, where each opening has an inner perimeter or configuration with at least one dimension that is smaller than a corresponding dimension of an arm that is arranged to be inserted therethrough, such that a friction locking is created once the arm has been inserted through the opening. The first mesh panel and the second mesh panel are preferably attached or connected to each other or the first mesh panel and the second mesh panel is made from a single piece preferably with a waist or a midsection separating the first and second mesh panel.

Here, it should be appreciated that according to the invention, each arm has a length that is relatively long, such that the arm is easy to handle for a doctor, who inserts the arm of a first mesh panel into a corresponding opening in a second mesh panel, i.e. the relatively long arm length provides by itself a user-friendliness since there is no need for the doctor to exactly determine how far the arm should be inserted through the opening before the breast implant is in position between the mesh panels. It is simply to insert a portion, e.g. a third or a half of the length, of each arm, place the breast implant in the space thereby created, and then tighten the arms, i.e. pull them further through the openings. Further, by providing arms with relatively long lengths, a large interval of implant sizes and shapes can be accommodated within one size of the mesh support device, which eliminates or at least reduces the need for keeping a large variety of mesh support devices in store.

According to embodiments of the invention, a mesh support device can comprise more than two arms, such that a first mesh panel further comprises a third arm and a fourth arm and a second mesh panel further comprises a third opening, which is arranged to receive the third arm, and a fourth opening, which is arranged to receive the fourth arm.

According to embodiments of the invention, the first and the second arm are arranged essentially perpendicular to the first and second side respectively.

For all embodiments of a mesh support device it is possible to arrange the mesh support device such that a first mesh panel is made from a first material and a second mesh panel is made from a second material, the second material being different from the first material. In this case, the first and/or second materials can optionally be two bio-degradable materials having different degradation times.

As an alternative, which also applies to all embodiments presented herein, a mesh support device can be arranged such that a first mesh panel and a second mesh panel are cut out from the same piece of mesh material. In this case, the mesh support device can further be arranged such that also first and second arms are cut out from the same piece of mesh material. This feature provides for an efficient manufacturing of mesh support devices according to the invention, and to further provide for a material-saving manufacturing the mesh support device can be arranged such that a first arm extends generally along a first side of a first mesh panel and a second arm extends generally along a second, opposite side of the first mesh panel. Also in these cases, the mesh material can be a bio-degradable mesh material.

BRIEF DESCRIPTION OF THE DRAWINGS

The invention will be described below with reference to the appended drawings, wherein same or similar elements have been given the same reference numerals, and.

DETAILED DESCRIPTION OF PREFERRED EMBODIMENTS

Figure 1A:
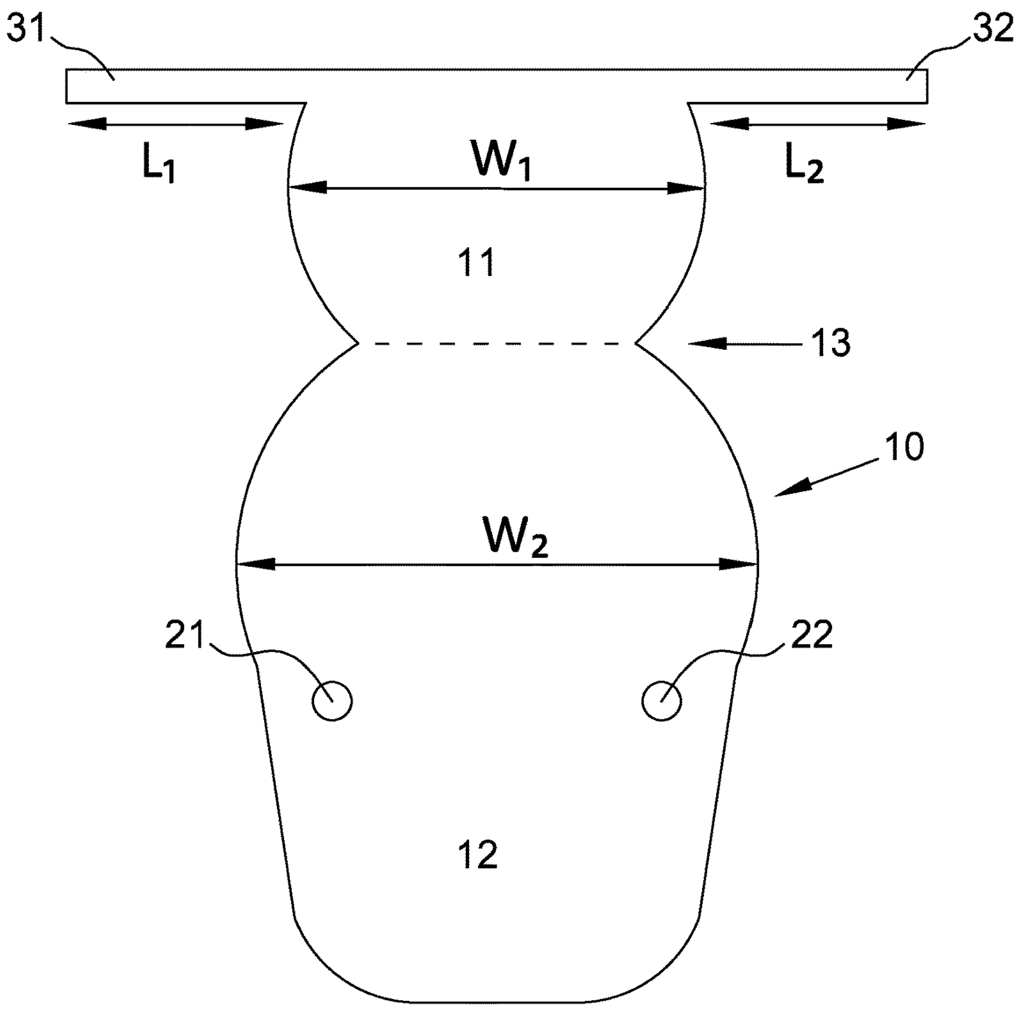
FIG. 1*a* illustrates schematically a front view of a first embodiment of a mesh support device according to the present invention.

In the figures, same, similar or corresponding elements have been given the same reference numerals.

FIG. 1*a* illustrates in front view a first embodiment of a mesh support device 10 according to the present invention. The mesh support device 10 comprises a first mesh panel 11 having a largest width $W_1$ and a second mesh panel 12 having a largest width $W_2$, where the latter is provided with a first opening 21 and a second opening 22 and is in this particular embodiment larger, i.e. has a larger area, than the first mesh panel 11. The first mesh panel 11 is provided with a first arm 31, which extends out from the first panel 11 on a first side (on the left-hand side in FIG. 1*a*) of the first mesh panel 11, and a second arm 32, which extends out from the first panel 11 on a second side (on the right-hand side in FIG. 1*a*) of the first mesh panel 11, so that the arms 31, 32 project on opposite sides of the first mesh panel 11. As will be discussed below, the mesh panels 11, 12 can have virtually any shape and are in this embodiment divided or separated (but not physically separated) by a waist or midsection 13. The device is configured to enclose or encapsulate a breast implant when the first and second arm are arranged in the first and second opening respectively. In one embodiment the width of either the first mesh panel or the second mesh panel is larger than the other. In another embodiment the area of either the first mesh panel or the second mesh panel is larger than the other. This provides for a better enclosure of the breast implant and thereby better support.

Further, the first arm 31 has a length $L_1$ and the second arm 32 has length $L_2$. According to the invention, the arm lengths $L_1$ and $L_2$ are relatively long, and depend in practice on the size of the particular breast implant that the mesh support device 10 is intended to support. The size of the mesh support device 10, i.e. the areal size of the first mesh panel 11 and the areal size of the second mesh panel 12, depends also on the size of the breast implant that is going to be used together with the support device 10, and here the size of the mesh support device 10 is characterized by the widths $W_1$ and $W_2$, respectively.

To achieve the special advantages with a mesh support device 10 according to the invention, the arms 31 and 32 are relatively long, but to not impair neither the user-friendliness nor the manufacturing efficiency should not be excessively long, and according to the present invention their lengths should be chosen such that 30 mm≤$L_1$≤210 mm, and more preferably 70 mm≤$L_1$≤180 mm, and most preferably 110 mm≤$L_1$≤150 mm; and 30 mm≤$L_2$≤210 mm, and more preferably 70 mm≤$L_2$≤180 mm, and most preferably 110 mm≤$L_2$≤150 mm. In this particular embodiment, there are two arms 31 and 32 provided on the first panel 11, but—as will be seen below—more arms, e.g. four or six arms, could be arranged. The first arm 31 and the second arm 32 have typically the same length ($L_1$=$L_2$), but it is within the scope of the invention that the lengths $L_1$ and $L_2$ are different ($L_1$≠$L_2$) as long as $L_1$ and $L_2$ fulfill their respective length intervals as given above.

Figure 1B:
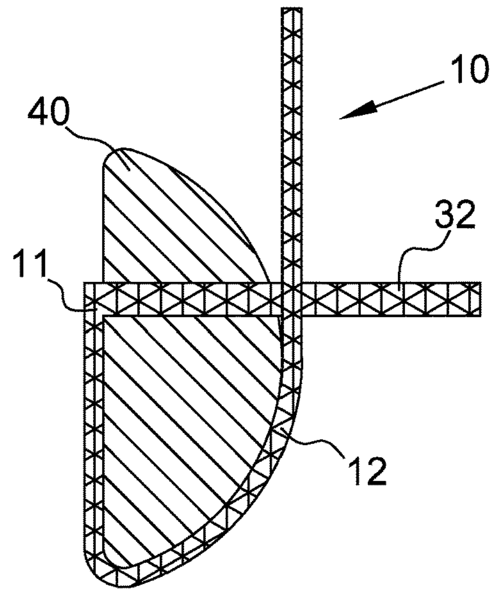
FIG. 1*b* illustrates in sideview a breast implant placed in the mesh support device of FIG. 1*a* in a first phase.

In FIG. 1*b*, the mesh support device 10 is schematically illustrated in sideview with a breast implant 40 positioned between the first mesh panel 11 and the second mesh panel 12; and it can in particular be seen that the first and second panels 11, 12 have been brought to lay or be arranged opposite each other such that a receiving space has been created therebetween. In practice, the mesh support device 10 has been gently folded or bent at the waist or midsection 13 such that the first and second mesh panels 11, 12 have been moved to a position opposite each other. With the first and second mesh panels 11, 12 in an opposite configuration, the first arm 31 has then been inserted through the first opening 21 and the second arm 32 has been inserted through the second opening 22 such that a space has been created between the first mesh panel 11 and the second mesh panel 12, in which space the breast implant 40 has been placed. By providing relatively long arms 31, 32, it is easy for a doctor to first insert, e.g., the first arm 31 into and partly through the first opening 21, and then insert the second arm 32 into and partly through the second opening 22 without risking that the first arm 31 during the subsequent operation retracts back out from the first opening 21. By providing long arms 31, 32, a large variety of breast implant sizes can be accommodated and supported with one size of a mesh support device. The long arms 31, 32 also provide extra mesh material that can be attached and anchored, e.g. by sewing or stitching, to a patient's breast tissue, as will be thoroughly discussed in conjunction with FIG. 5 below.

Figure 1C:
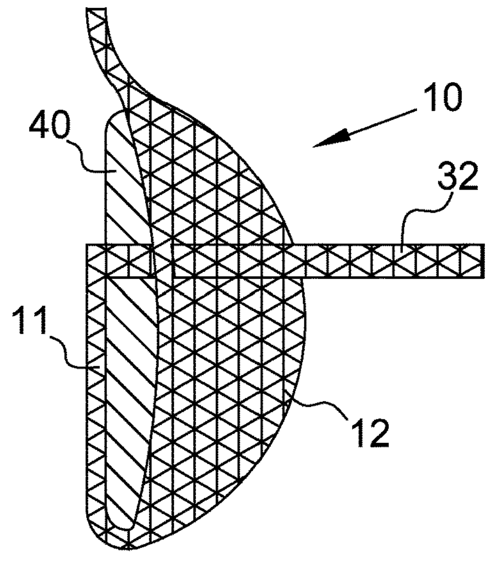
FIG. 1*c* illustrates the breast implant and the support device in a second phase.

In the configuration shown in FIG. 1*b*, the arms 31, 32 have only been inserted a certain, limited distance through the respective openings 21, 22, e.g. a third or one half of the length of an arm can have been brought through a corresponding opening, such that a spacious receiving space is created, in which it is easy to place the breast implant 40. In FIG. 1*c*, a subsequent configuration is shown, where the arms 31, 32 have been tightened around the breast implant 40, i.e. the arms 31, 32 have been inserted further through the openings 21, 22 such that major portions of the lengths $L_1$ and $L_2$ have passed the first opening 21 and the second opening 22, respectively. By this tightening operation, the second mesh panel 12 is draped over and encloses the breast implant 40, which thereby is firmly held in place by the mesh support device 10.

Further, to keep the breast implant 40 securely in place, the first arm 31 and the corresponding first opening 21 as well as the second arm 32 and the corresponding second opening 22 are dimensioned such that a friction locking is created once one arm 31 or 32 has been inserted through a corresponding opening 21 or 22. In practice, an arm 31 or 32 is gently folded or rolled around its longitudinal axis before its outer end is threaded through a corresponding opening 21 or 22, which, when the arm 31 or 32 thereafter strives to resume its original shape, creates the friction locking that prevents the arm 31 or 32 from moving back out from the corresponding opening 21 or 22 once it has been threaded therethrough. As can be seen in FIG. 1*a*, the first and second openings 21 and 22 have the shapes of circular holes 21, 22, whose diameters are smaller than the widths of the arms 31, 32. To provide for a secure and reliable friction locking the first arm 31 can have width in the interval of 5 mm to 30 mm, and also the second arm 32 can have a width in the interval of 5 mm to 30 mm. However, the widths chosen for the first and second arms 31, 32 depend on the size and also shape of the corresponding openings 21, 22.

From FIGS. 1*b* and 1*c* it can further be inferred that the first mesh panel 11 is a backside panel, which is intended to lay in contact with the flat backside of the breast implant 40. It can also be seen that the relatively larger area of the second mesh panel 12, which consequently is a frontside panel intended to be in contact with the convex frontside of the breast implant 40, ensures that the breast implant 40 is well covered and enclosed by the second mesh panel 12. Preferably the area of the second mesh panel 12 is so large that extra mesh material is provided around the outer rim of the breast implant 40, whereby the extra mesh material can be used for securing the support device 10 in the breast tissue of the human patient. In one embodiment the width of the first mesh panel is less than the width of the second mesh panel, $W_1$<$W_2$. In another embodiment the area of the second mesh panel is larger than the area of the first mesh panel. This feature will be further described in conjunction with FIG. 5 below. In this embodiment, the first mesh panel 11 has a generally circular shape with a top segment removed and a bottom segment removed, and the second mesh panel 12 has also a generally circular shape with a top segment removed and with a prolonged or extended bottom portion. The specific shapes of the first and second mesh panels 11, 12 are, however, not overly important for practicing the present invention as long as a breast implant is sufficiently enclosed by the support device in question.

Figure 2A:
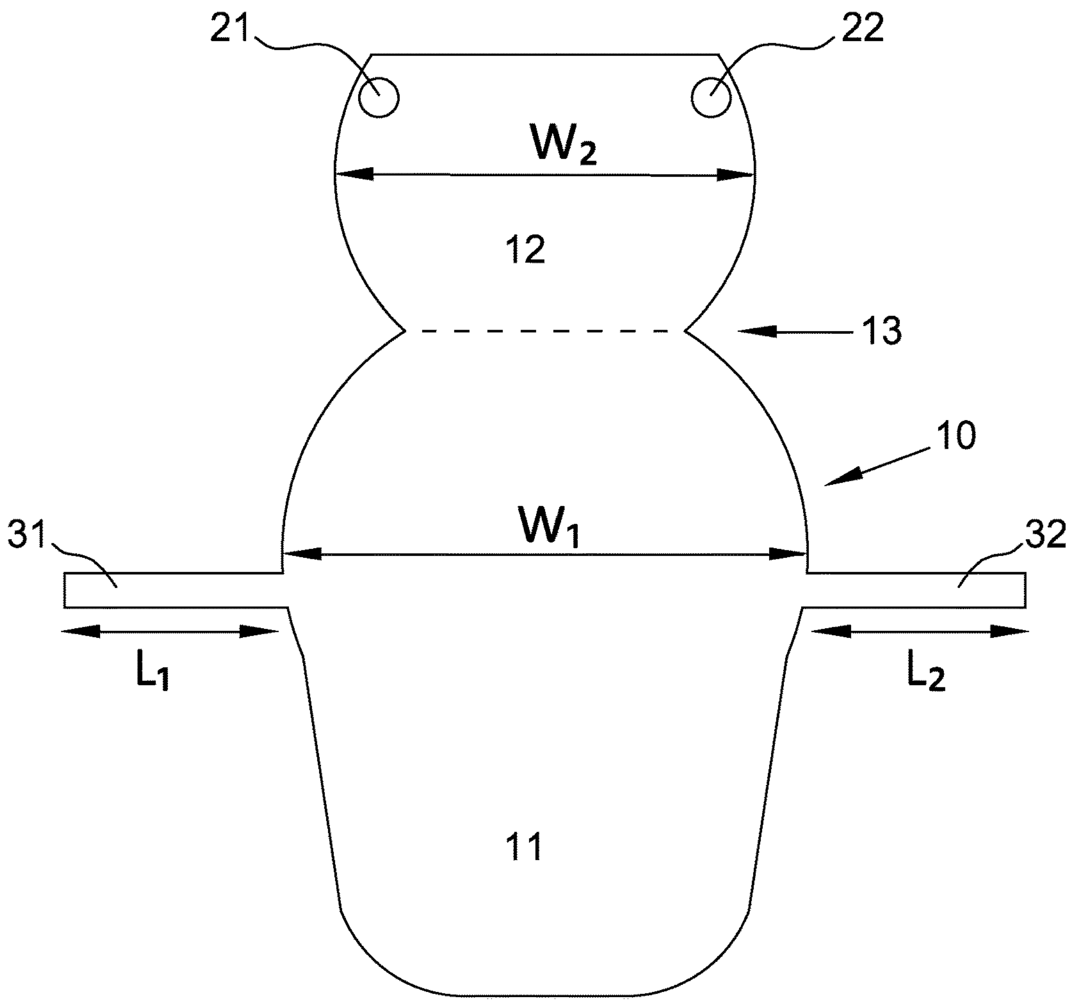
FIG. 2*a* illustrates schematically a front view of a second embodiment of a mesh support device according to the present invention.

FIG. 2*a* illustrates in front view a second embodiment of a mesh support device 10 according to the present invention. The mesh support device 10 comprises a first mesh panel 11 having a largest width $W_1$ and a second mesh panel 12 having a largest width $W_2$, where the latter is provided with a first opening 21 and a second opening 22 and is in this particular embodiment smaller, i.e. has a smaller area, than the first mesh panel 11. The first mesh panel 11 is provided with a first arm 31, which extends out from the first panel 11 on a first side (on the left-hand side in FIG. 2*a*) of the first mesh panel 11, and a second arm 32, which extends out from the first panel 11 on a second side (on the right-hand side in FIG. 2*a*) of the first mesh panel 11, so that the arms 31, 32 project on opposite sides of the first mesh panel 11. As will be discussed below, the mesh panels 11, 12 can have virtually any shape and are in this embodiment divided or separated (but not physically separated) by a waist or midsection 13.

Further, the first arm 31 has a length $L_1$ and the second arm 32 has length $L_2$. According to the invention, the arm lengths $L_1$ and $L_2$ are relatively long, and depend in practice on the size of the particular breast implant that the mesh support device 10 is intended to support. The size of the mesh support device 10, i.e. the areal size of the first mesh panel 11 and the areal size of the second mesh panel 12, depends also on the size of the breast implant that is going to be used together with the support device 10, and here the size of the mesh support device 10 is characterized by widths $W_1$ and $W_2$, respectively.

To achieve the special advantages with a mesh support device 10 according to the invention, the arms 31 and 32 are relatively long, but to not impair neither the user-friendliness nor the manufacturing efficiency should not be excessively long, and according to the present invention their lengths should be chosen such that 30 mm$\le L_1 \le$210 mm, and more preferably 70 mm$\le L_1 \le$180 mm, and most preferably 110 mm$\le L_1 \le$150 mm; and 30 mm$\le L_2 \le$210 mm, and more preferably 70 mm$\le L_2 \le$180 mm, and most preferably 110 mm$\le L_2 \le$150 mm. In this particular embodiment, there are two arms 31 and 32 provided on the first panel 11, but—as will be seen below—more arms, e.g. four or six arms, could be arranged. The first arm 31 and the second arm 32 have typically the same length ($L_1$=$L_2$), but it is within the scope of the invention that the lengths $L_1$ and $L_2$ are different ($L_1 \neq L_2$) as long as $L_1$ and $L_2$ fulfill their respective length intervals as given above.

Figure 2B:
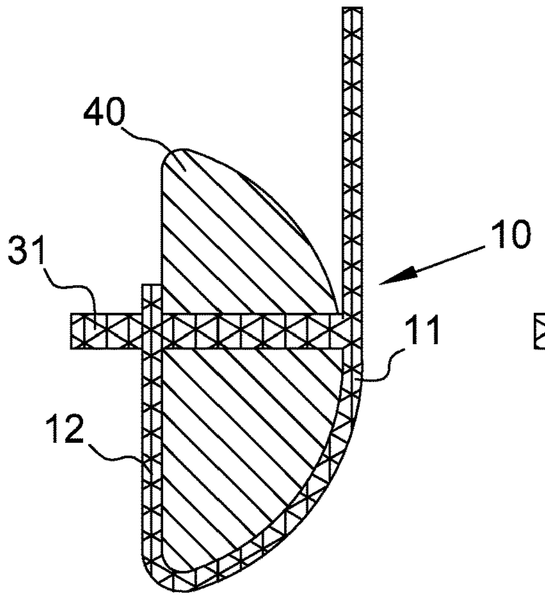
FIG. 2*b* illustrates in sideview a breast implant placed in the mesh support device of FIG. 2*a* in a first phase.

In FIG. 2*b*, the mesh support device 10 is schematically illustrated in sideview with a breast implant 40 positioned between the first mesh panel 11 and the second mesh panel 12; and it can in particular be seen that the first and second panels 11, 12 have been brought to lay opposite each other such that a receiving space has been created therebetween. In practice, the mesh support device 10 has been gently folded or bent at the waist or midsection 13 such that the first and second mesh panels 11, 12 have been moved to a position opposite each other. With the first and second mesh panels 11, 12 in an opposite configuration, the first arm 31 has then been inserted through the first opening 21 and the second arm 32 has been inserted through the second opening 22 such that a space has been created between the first mesh panel 11 and the second mesh panel 12, in which space the breast implant 40 has been placed. By providing relatively long arms 31, 32, it is easy for a doctor to first insert, e.g., the first arm 31 into and partly through the first opening 21, and then insert the second arm 32 into and partly through the second opening 22 without risking that the first arm 31 during the subsequent operation retracts back out from the first opening 21. By providing long arms 31, 32, a large variety of breast implant sizes can be accommodated and supported with one size of a mesh support device. The long arms 31, 32 also provide extra mesh material that can be attached and anchored, e.g. by sewing or stitching, to a patient's breast tissue, as will be thoroughly discussed in conjunction with FIG. 5.

Figure 2C:
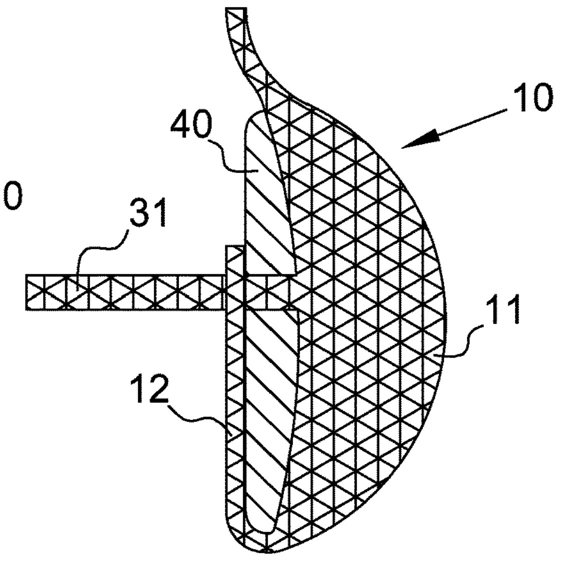
FIG. 2*c* illustrates the breast implant and the support device in a second phase.

In the configuration shown in FIG. 2*b*, the arms 31, 32 have only been inserted a certain, limited distance through the respective openings 21, 22, e.g. a third or one half of the length of an arm can have been brought through a corresponding opening, such that a spacious receiving space is created, in which it is easy to place the breast implant 40. In FIG. 2*c*, a subsequent configuration is shown, where the arms 31, 32 have been tightened around the breast implant 40, i.e. the arms 31, 32 have been inserted further through the openings 21, 22 such that major portions of the lengths $L_1$ and $L_2$ have passed the first opening 21 and the second opening 22, respectively. By this tightening operation, the second mesh panel 12 is draped over and encloses the breast implant 40, which thereby is firmly held in place by the mesh support device 10.

Further, to keep the breast implant 40 securely in place, the first arm 31 and the corresponding first opening 21 as well as the second arm 32 and the corresponding second opening 22 are dimensioned such that a friction locking is created once one arm 31 or 32 has been inserted through a corresponding opening 21 or 22. In practice, an arm 31 or 32 is gently folded or rolled around its longitudinal axis before its outer end is threaded through a corresponding opening 21 or 22, which, when the arm 31 or 32 thereafter strives to resume its original shape, creates the friction locking that prevents the arm 31 or 32 from moving back out from the corresponding opening 21 or 22 once it has been threaded therethrough. As can be seen in FIG. 2*a*, the first and second openings 21 and 22 have the shapes of circular holes 21, 22, whose diameters are smaller than the widths of the arms 31, 32. To provide for a secure and reliable friction locking the first arm 31 can have width in the interval of 5 mm to 30 mm, and also the second arm 32 can have a width in the interval of 5 mm to 30 mm. However, the widths chosen for the first and second arms 31, 32 depend on the size and also shape of the corresponding openings 21, 22.

From FIGS. 2*b* and 2*c* it can further be inferred that the second mesh panel 12 is a backside panel, which is intended to lay in contact with the essentially flat backside of the breast implant 40. It can also be seen that the relatively larger area of the first mesh panel 11, which consequently is a frontside panel intended to be in contact with the convex frontside of the breast implant 40, ensures that the breast implant 40 is well covered and enclosed by the first mesh panel 11. Preferably the area of the first mesh panel 11 is so large that extra mesh material is provided around the outer rim of the breast implant 40, whereby the extra mesh material can be used for securing the support device 10 in the breast tissue of the human patient. This feature will be further described in conjunction with FIG. 5 below. In this embodiment, the second mesh panel 12 has a generally circular shape with a top segment removed and a bottom segment removed, and the first mesh panel 11 has also a generally circular shape with a top segment removed and with a prolonged or extended bottom portion. The specific shapes of the first and second mesh panels 11, 12 are, however, not overly important for practicing the present invention as long as a breast implant is sufficiently enclosed by the support device in question.

A comparison of FIG. 1*a* and FIG. 2*a* reveals that according to the invention, the arms can be arranged at a first mesh panel, which, when the support device is in use, either will constitute a front side or a backside, and that the corresponding openings can be arranged in a second mesh panel, which, when the support device is in use, will constitute the opposite and complementary side.

Figure 3:
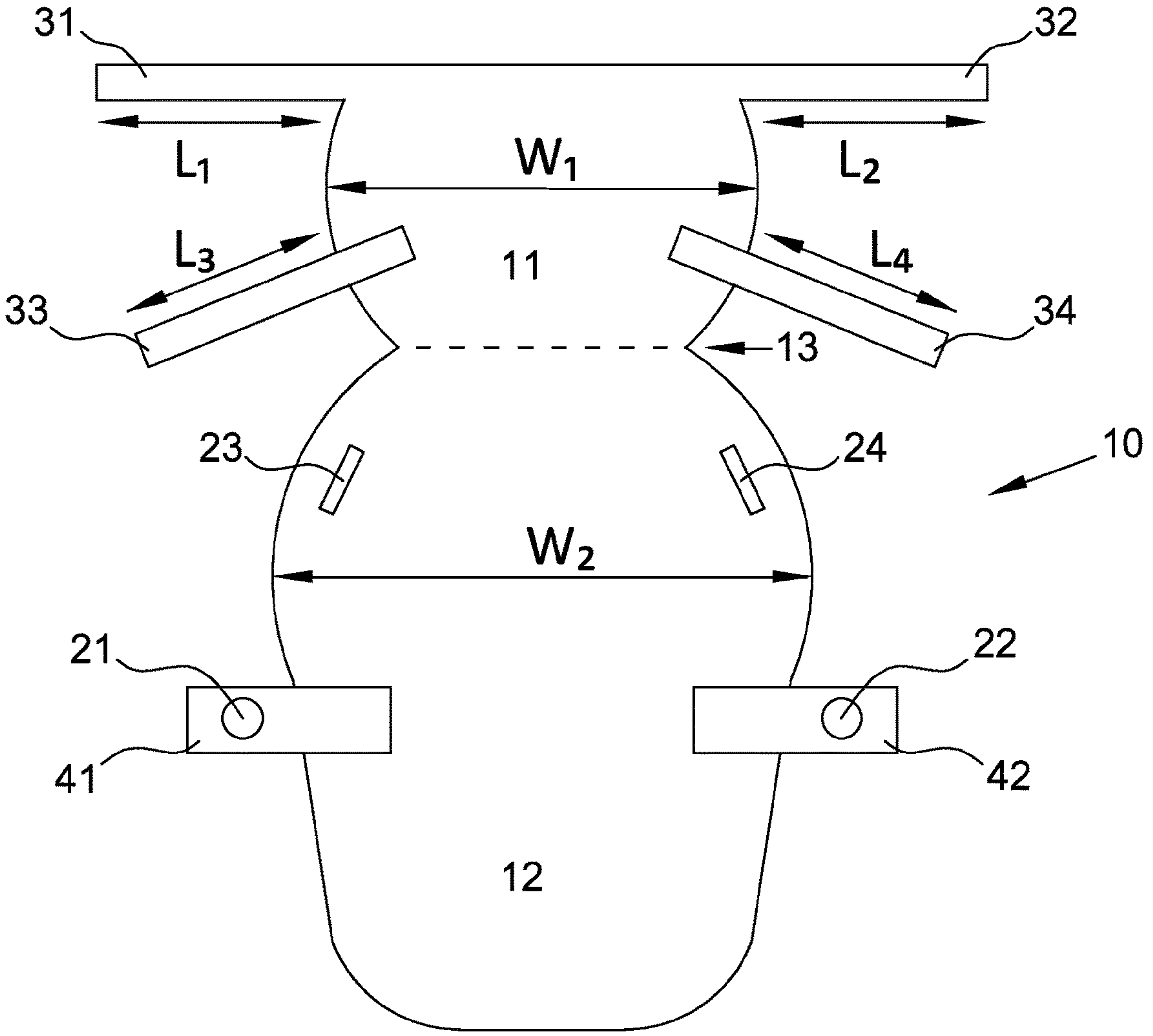
FIG. 3 illustrates schematically a front view of a third embodiment of a mesh support device according to the present invention.

FIG. 3 illustrates schematically a third embodiment of a mesh support device 10 according to the present invention. The mesh support device 10 comprises a first mesh panel 11 and a second mesh panel 12, where the latter is provided with a first opening 21, a second opening 22, a third opening 23 and a fourth opening 24 and is in this particular embodiment larger, i.e. has larger area, than the first mesh panel 11. The first mesh panel 11 is provided with a first arm 31 and a third arm 33, which extend out from the first panel 11 on a first side (on the left-hand side in FIG. 3) of the first mesh panel 11, and a second arm 32 and a fourth arm 34, which extend out from the first panel 11 on a second side (on the right-hand side in FIG. 3) of the first mesh panel 11, so that the first and third arms 31, 33 and the second and fourth arms 32, 34 project on opposite sides of the first mesh panel 11. As was discussed above, the mesh panels 11, 12 can have virtually any shape and are in this embodiment divided or separated (but not physically separated) by a waist or midsection 13.

Further, the first arm 31 has a length $L_1$, the second arm 32 has length $L_2$, the third arm 33 has a length $L_3$ and the fourth arm 34 has a length $L_4$. According to the invention, the arm lengths $L_1$, $L_2$, $L_3$ and $L_4$ are relatively long, and depend in practice on the size of the particular breast implant that the mesh support device 10 is intended to support. The size of the mesh support device 10, i.e. the size of the first mesh panel 11 and the size of the second mesh panel 12, depends also on the size of the breast implant that is going to be used together with the support device 10, and here the size of the mesh support device 10 is characterized by widths $W_1$ and $W_2$, respectively.

To achieve the special advantages with a mesh support device 10 according to the invention, the arms 31, 32, 33 and 34 are relatively long, but to not impair neither the user-friendliness nor the manufacturing efficiency should not be excessively long, and according to the present invention their lengths should be chosen such that 30 mm$\leq L_1 \leq$210 mm, and more preferably 70 mm$\leq L_1 \leq$180 mm, and most preferably 110 mm$\leq L_1 \leq$150 mm; and 30 mm$\leq L_2 \leq$210 mm, and more preferably 70 mm$\leq L_2 \leq$180 mm, and most preferably 110 mm$\leq L_2 \leq$150 mm; and 30 mm$\leq L_3 \leq$210 mm, and more preferably 70 mm$\leq L_3 \leq$180 mm, and most preferably 110 mm$\leq L_3 \leq$150 mm; and 30 mm$\leq L_4 \leq$210 mm, and more preferably 70 mm$\leq L_4 \leq$180 mm, and most preferably 110 mm$\leq L_4 \leq$150 mm. In this particular embodiment, there are four arms 31, 32, 33 and 34 provided at the first panel 11, but other numbers of arms could have been arranged. The first arm 31 and the second arm 32 have typically the same length ($L_1$=$L_2$), and the third arm 33 and the fourth arm 34 have typical the same length ($L_3$=$L_4$), but it is within the scope of the invention that the all lengths are different ($L_1 \neq L_2 \neq L_3 \neq L_4$) as long as the arms fulfill their respective length intervals.

The third embodiment of a medical support device 10 shown in FIG. 3, has four arms instead of two arms as was the case for the first embodiment and the second embodiment depicted in FIGS. 1*a-c* and FIGS. 2*a-c*, respectively. In FIG. 3 it is further illustrated that according to the invention, an arm can be made from the same piece of mesh material as a first mesh panel, i.e. the arms and the first mesh panel are cut out from the same piece of mesh material. This is the case for the first and second arms 31, 32 in the embodiment shown in FIG. 3. To use the same piece of mesh material for the arms and the first mesh panel provides for an efficient manufacturing procedure. The third and fourth arms 33, 34 are, however, instead arranged as separate arms 33, 34, which have been attached, e.g. by sewing, stitching or gluing, at the first mesh panel 11. To arrange arms as separate elements provides for the possibility to have one material in the arms and another, different material in the first mesh panel. The material of the arms can thereby, for example, be chosen to provide for a good strength and/or a good friction locking of the arms within the corresponding openings, while the material selected for the first mesh panel provides for, e.g., good flexibility and/or tissue integration. However, for manufacturing reasons, for example to provide for an efficient use of material, also separate arms, which are attached, e.g. by sewing, stitching or gluing, to a first mesh panel, can be made from the same type mesh material, but are then not cut out from the same piece of mesh material. For all embodiments of the present invention, arms can either be provided as arms which are integral with a first mesh panel, i.e. are cut out from the same piece of mesh material, or arms can be provided as separate elements, which are attached to a first mesh panel. In the latter case, the arms and the first panel can be made from the same type of material or from different materials.

FIG. 3 illustrates further that the third and fourth openings 23, 24 have the shapes of slits, which can provide for a secure friction locking when the third and fourth arms 33, 34 have been inserted therethrough. The first and second openings 21, 22 are on the other hand arranged on tabs 41, 42, where a first tab 41 projects out on a first side (on the left-hand side in FIG. 3) from the general contour of the second mesh panel 12 and a second tab 42 projects out on a second, opposite side (on the right-hand side in FIG. 3) from the general contour of the second mesh panel 12. The arrangement of openings in tabs that project out from opposite sides of the general perimeter of a mesh panel can provide for a receiving space whose shape is well adapted to the shape of breast implant that is to be positioned therein.

Each threading step can be preceded by same manipulation of the arm to be threaded. The arm can, for example, be folded or rolled along its longitudinal extension, to thereby create a more solid and more pointed arm. To facilitate the threading operation, the arms can also be made pointed. As an alternative or supplement, an arm, i.e. preferably an outer end thereof, can further be provided with a stiffener, which can comprise hardening of the material of the outer end of the arm, e.g. by a heat treatment, or a coating can be arranged on the outer end of the arm, or a small object, such as a rod or pin, can be attached to the outer end of an arm. All of these and similar means and measures provided to stiffen the outer end of an arm are herein encompassed in the term “stiffener”.

The tabs 41, 42 can be made integral with the second mesh panel 12, i.e. the tabs 41, 42 and the second mesh panel 12 are cut out from the same piece of mesh material. As an alternative, it is, however, possible to arrange the tabs 41, 42 as separate elements on the second mesh panel 12. The tabs 41, 41 can then be attached, e.g. by sewing, stitching or gluing, on the second mesh panel 12. To arrange the openings 23, 24 in tabs 41, 42, which are arranged as separate elements, provide for the possibility to have one material in the tabs 41, 42 and another, different material in the second mesh panel 12. The material of a tab, and consequently the material that surrounds the opening therein, can thereby, for example, be chosen to provide for a good strength and/or a good friction locking of the arms in the corresponding openings, while the material selected for the second mesh panel provides for good flexibility and/or tissue integration. For all embodiments of the present invention, openings can either be provided in a second mesh panel, i.e. the openings are cut, stamped, drilled or punched out in the second mesh panel and are positioned inside the general contour of the second mesh panel, or openings can be provided in tabs, which project out from the general contour of the second mesh panel and which either are integral with the second mesh panel, i.e. the tabs and the second mesh panel are cut out from the same piece of mesh material, or which are arranged as separate elements and are attached to the second mesh panel by, for example, sewing, stitching or gluing. In the latter case, the tabs and the second mesh panel can be made from the same type of material or from different materials.

Figure 4:
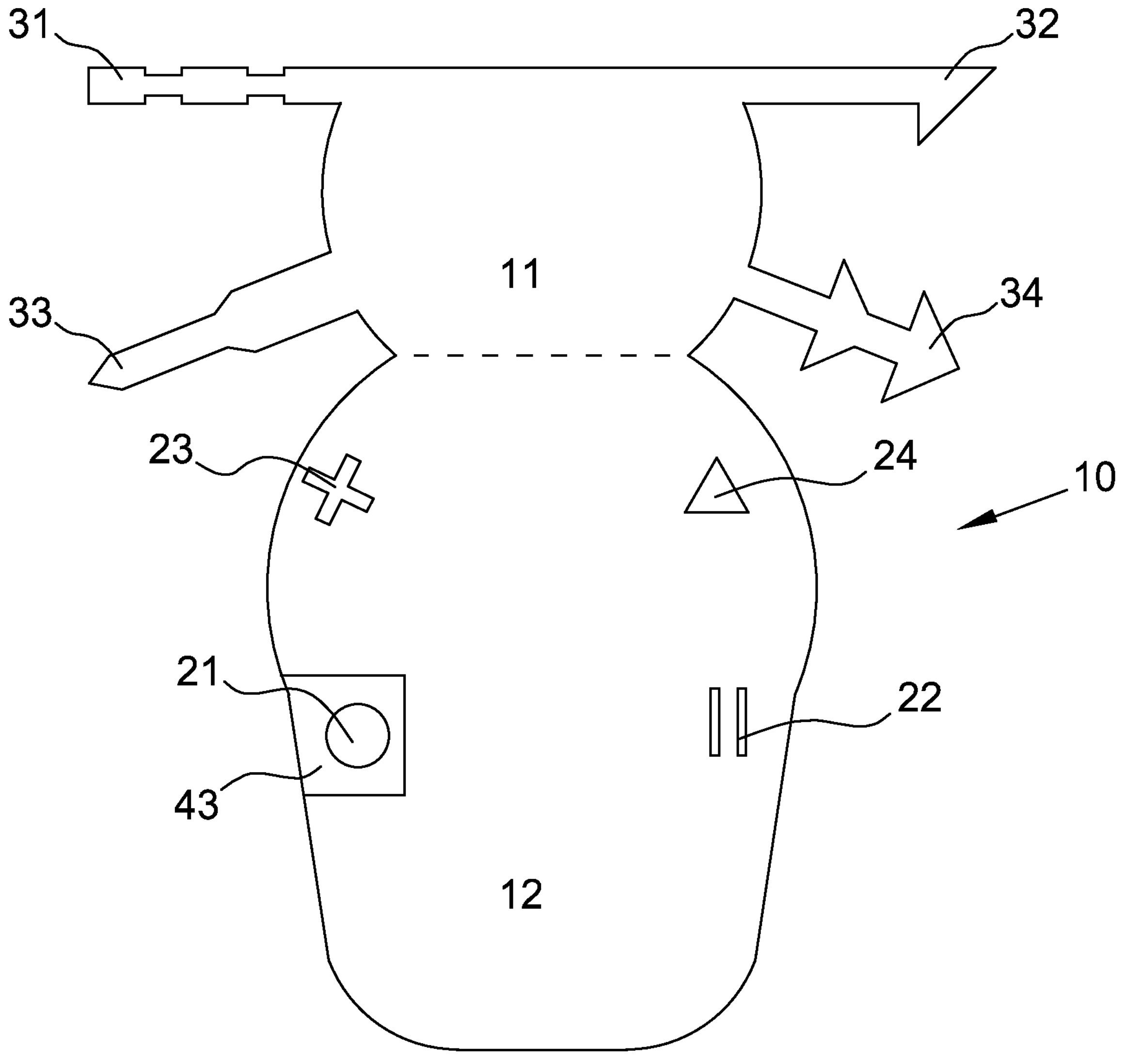
FIG. 4 illustrates schematically a front view of an illustrative and exemplifying fourth embodiment of a mesh support device according to the present invention.

FIG. 4 illustrates and exemplifies different shapes of openings in a second mesh panel 12 of a support device 10 according to the invention. It can be seen that a first opening 21 is provided in the shape of a circular hole, whose circumference has been reinforced with an extra patch 43 of material that has been attached to the second mesh panel 12, and that a second opening 22 is arranged in the shape of a double-slit, which comprises an inner slit and an outer slit and into which a second arm 32 is to be inserted, such that the second arm 32 is first introduced into the inner slit and then back out again through the outer slit. There is further a third opening 23 arranged in the shape of a cross, and a fourth opening 24 is arranged in the shape of an open triangle.

The support device 10 shown in FIG. 4 comprises further a first mesh panel 11, which comprises a first arm 31 provided with a number of indentations (here two indentations on each side). Once the first arm 31 has been inserted into the corresponding opening 21, the indentations will serve as ratchets that prevent the first arm 31 from moving back out from the opening 21. The first mesh panel 11 comprises a second arm 32 whose end is shaped as a semi-arrow, which is configured to prevent the second arm 32 from moving back out from the opening 22 once it has been inserted therethrough. A third arm 33 has a pointy end and is provided with a large inner width and a smaller outer width, to thereby provide for easy insertion through the opening 23 and a maximum of friction when the third arm 33 has been fully inserted through the opening 23. Lastly, a fourth arm 34 is shaped as double-arrow with two consecutive arrows which are configured to serve as an inner stop and an outer stop, whereby the inner stop is intended to be in operation when the fourth arm 34 has been fully inserted through the opening 24 (i.e. corresponding to the configuration shown in FIGS. 1*c* and 2*c*) and the outer stop is intended to be in operation when the fourth arm 34 has only been inserted a limited distance through an opening 24 (i.e. corresponding to the configuration shown in FIGS. 1*b* and 2*b*). In one embodiment the third and fourth arm are arranged essentially perpendicular to the first and the second side respectively. In another embodiment the third and fourth arm are arranged at a non-perpendicular angle from the first and second side respectively.

The main purpose of FIG. 4 is not to show a realistic embodiment of the present invention, where each arm and opening has a special, individual shape, but merely to show possible shapes and configurations of arms and openings in a mesh support device 10 according to the present invention; and FIG. 4 illustrates how the friction locking between an arm and an opening can be supplemented, enhanced and/or improved by different shapes and configurations. All of the different shapes of the arms and openings, respectively, can be used in all combinations and in all of the embodiments disclosed herein.

Figure 5:
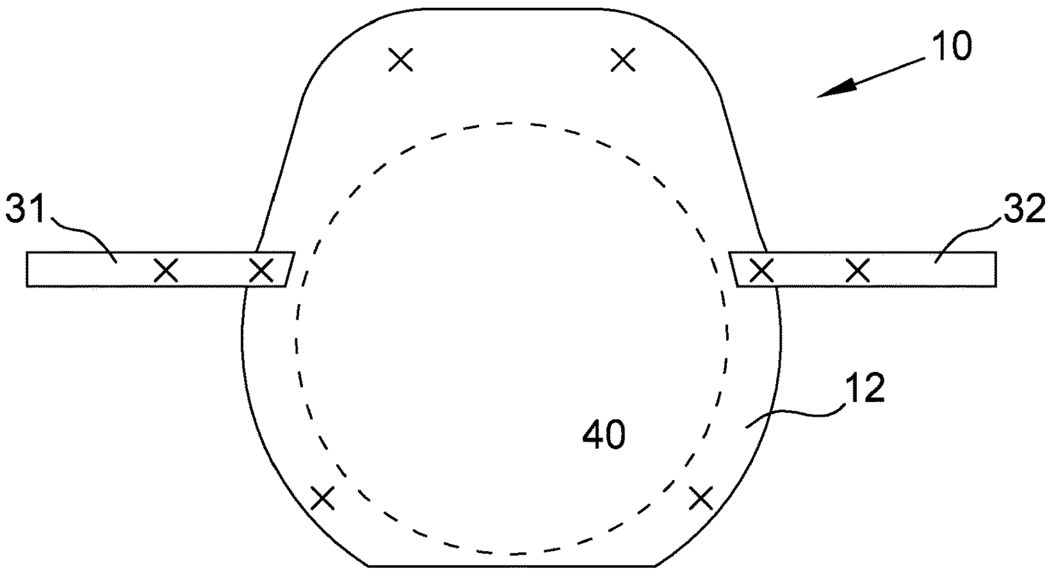
FIG. 5 illustrates schematically a front view of a mesh support device according to the invention with a breast implant placed therein.

FIG. 5 illustrates a front view of a mesh support device 10 with a breast implant 40 in place, and it can in particular be seen that a second mesh panel 12 serves as a front panel and covers the breast implant 40 and that a first arm 31 and a second arm 32, which are arranged at a first mesh panel 11 (not visible in FIG. 5), have been threaded through corresponding openings in the second mesh panel 12. The first and second arms 31, 32, which according to the invention are relatively long, can now advantageously be used for securing the mesh support device 10 in a patient's breast tissue. Further, by selecting the size of mesh support device 10, and in particular by selecting the size of the mesh panel that will serve as front panel, in such a way that extra material is provided around at least parts of the breast implant 40, this extra material can be used to secure, e.g. by stapling, sewing or stitching, the mesh support device 10 in the patient's breast tissue at, for example, the positions marked with crosses. It can further be noted that when the arms 31, 32 are secured in the breast tissue, the breast implant 40 is simultaneously further fixated within the mesh support device 10, i.e. as a supplement to the fixation that already has been accomplished be pulling the arms 31, 32 fully through the corresponding openings in the second mesh panel 12, such that the arms 31, 32 are held in place by friction locking created between the respective arm and the inner perimeter of the corresponding opening.

Thus, for all embodiments presented herein, the dimension(s) of an opening is (are) generally smaller than the corresponding dimension(s) of an arm that is configured to be inserted through the opening. Typically, some manipulation is therefore required to initially force the arm through the opening, and the arm can, for example, be gently folded or rolled along its longitudinal axis, to temporarily reduce its transverse extension, before the arms is threaded or pushed through the opening. To provide for a secure and reliable friction locking the first arm can have width in the interval of 5 mm to 30 mm, and also the second arm can have a width in the interval of 5 mm to 30 mm. However, the widths chosen for the first and second arms depend on the size and also shape of the corresponding openings. The correspond widths are applicable if more than two arms are arranged in a mesh panel.

As has been mentioned above, the arms of a first mesh panel can be arranged integral with the first mesh panel, i.e. the arms and first mesh panel are cut out from the same piece of mesh material, or the arms can be arranged as separate elements which are attached to the first mesh panel. In the latter case, the arms can be made from the same sort of material as the first mesh panel, or the arms and the first mesh panel can be made from different materials. Similarly, for all embodiments presented herein, a first mesh panel can be made from a first material and a second mesh panel can be made from a second material, which is different from the first material. In this case, the first mesh panel and the second mesh panel are joined together, e.g. by sewing, at a position that will correspond to a midsection. If, for example, the first mesh panel is intended to constitute the front panel, the first material can be a flexible material that adapts to the convex shape of the front side of a breast implant, while the second material is a material that promotes tissue integration at the backside of the breast implant. Obviously, the opposite applies if the second mesh panel is intended to constitute the front panel, while the first mesh panel is intended to constitute the back panel.

However, as an alternative, which also applies for all embodiments presented herein, a first mesh panel and a second mesh panel can be made as an integral unit, which here means that the first mesh panel and the second mesh panel are arranged as one piece of mesh material, i.e. a front panel and a back panel are created by folding the piece of mesh material at a midsection. This latter case, when the first mesh panel and the second mesh panel are made from the same piece of mesh material, provides for a very efficient and material-saving manufacturing, as is illustrated in FIG. 6.

Figure 6:
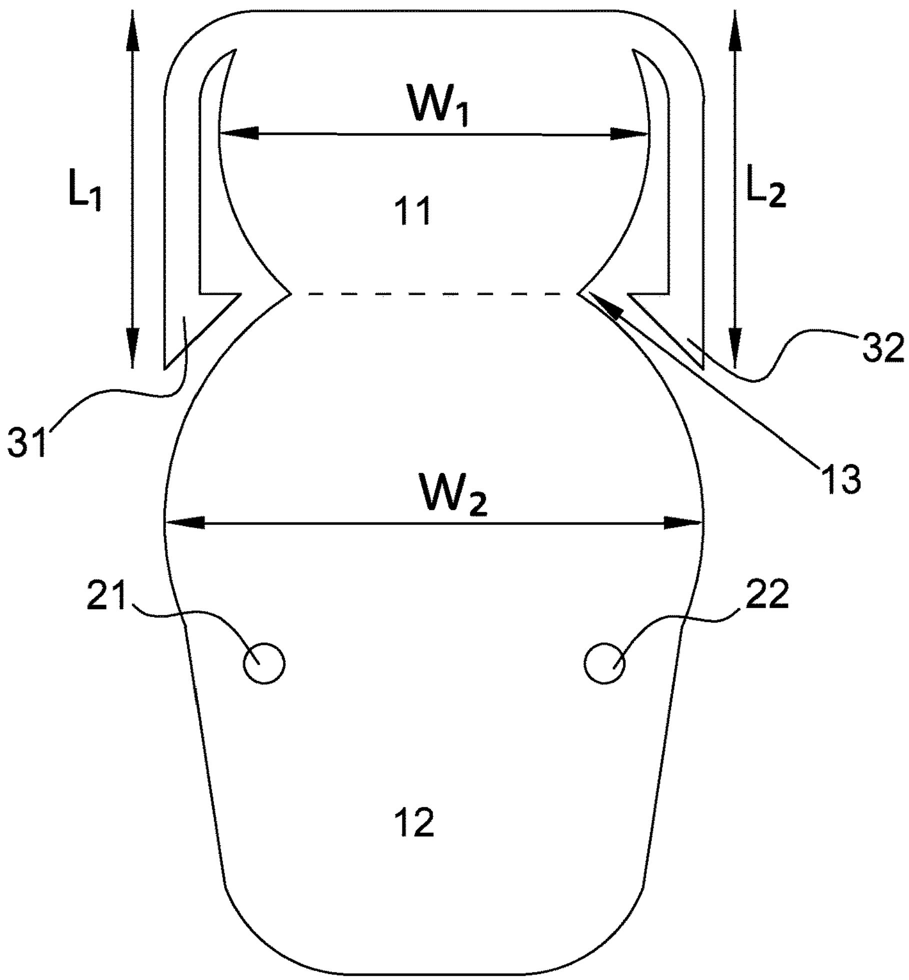
FIG. 6 illustrates schematically a front view of a fifth embodiment of a mesh support device according to the present invention.

FIG. 6 illustrates a fifth embodiment of a mesh support device 10 according to the present invention, where the mesh support device 10 comprises a first mesh panel 11 having a largest width $W_1$ and a second mesh panel 12 having a largest width $W_2$. The first mesh panel 11 comprises a first arm 31, which is configured to be inserted through a first opening 21 provided in the second mesh panel 12, and a second arm 32, which is configured to be inserted through a second opening 22 provided in the second mesh panel 12, as has been described before. The first mesh panel 11 and the second mesh panel 12 are cut out from the same piece of mesh material; and to create a receiving space for a breast implant, the mesh support device 10 is folded or bent at the position of a waist or midsection 13. A special feature of the mesh support device 10 shown in FIG. 6 is that also the first and second arms 31, 32 are cut out from the same piece of mesh material, and rather than extending more or less transversally to the general extension of the mesh support device 10—something which has been the case for the arms described in conjunction with the previous embodiments and figures—the first and second arms 31 of this embodiment extend generally along the first mesh panel 11, to thereby provide for a manufacturing that makes efficient use of the available mesh material. A configuration wherein the first mesh panel, the second mesh panel and the arms are all cut out from the same piece of mesh material can be applied for all embodiments presented herein, and the arms can also be arranged generally along (rather than generally perpendicular to) a first mesh panel for all embodiments presented herein.

A mesh support device 10 can be made by means of any known knitting or weaving technique, and it is preferred that the mesh for the support device is made by a technique that prevents unraveling of the mesh support device 10. One example of such a knitting technique is warp-knitting, which is a family of knitting methods in which the yarn zigzags along the length of the fabric, i.e. following adjacent columns of knitting rather than a single row. By using a manufacturing method that prevents, or at least reduces the risk of, unraveling, the mesh support device can be more reliable anchored (e.g. stitched, sewed, sutured or stapled) to the human breast tissue during and after implantation of a breast implant. The openings of the embodiments presented herein can simply be provided by cutting or stamping, especially when the mesh is made by a technique that prevents unraveling.

In a preferred embodiment, the mesh of a mesh support device 10 is made from a degradable material, and preferably from a bio-degradable material, which means that the material in question can be resorbed by the human body. By using a degradable material, which degrades inside the body, complications that are known to sometimes be associated with permanent mesh products can be avoided. Examples of materials in the fibers or yarns that constitute the mesh of the mesh support device 10 are (a) resorbable polymers with a relatively short degradation time, and non-limiting examples are polymers or copolymers made from the monomer glycolide in pure form, or in combination with paradioxanone, lactide, trimethylene carbonate or caprolactone, or polymers or copolymers made from the monomer paradioxanone in its pure form, or in combination with lactide, trimethylene carbonate or caprolactone; or (b) resorbable polymers with a relative long degradation time, and non-limiting examples are polylactide and polyurethanes, e.g. polyureaurethanes, polyesterurethanes and polycarbonateurethanes; or (c) any combinations thereof.

As indicated above, several materials can be combined in a single mesh support device according to the present invention, and a suitable mesh is commercially available under the tradename TIGR® Matrix Surgical Mesh and is sold by the company Novus Scientific. This mesh, which is described in US9566370, US8083755 and US8016841, comprises two different polymers having different degradation times, and it is believed that the resulting gradual degradation can promote tissue integration of a mesh support device made by this particular mesh. However, although synthetic and degradable materials are believed to be advantageous, a mesh support device according to the present invention can be made from permanent (non-degradable, non-resorbable) synthetic materials or even from biological materials, and any combination thereof.

Although the present invention has been described with reference to specific embodiments, also shown in the appended drawings, it will be apparent to those skilled in the art that many variations and modifications can be done within the scope of the invention as described in the specification and defined with reference to the claims below.

The invention claimed is:

1. A breast implant assembly comprising:
- a breast implant having a convex frontside and an essentially flat backside; and
- a mesh support device comprising:
  - a first mesh panel comprising:
    - a first arm located at a first side of the first mesh panel, and
    - a second arm located at a second side of the first mesh panel opposite the first side, wherein:
    - the first arm and the second arm extend from the first mesh panel in substantially opposite directions; and
  - a second mesh panel connected to the first panel, the second mesh panel comprising:
    - a first opening configured to receive the first arm, and
    - a second opening configured to receive the second arm; wherein:
  - the first mesh panel and the second mesh panel are connected at a waist having a width less than a width of the first mesh panel and a width of the second mesh panel; and
  - an area and/or the width of the second mesh panel is greater than an area and/or the width of the first mesh panel; wherein:
- the waist is located at a bottom of the breast implant, and the support device is folded at the waist such that the first mesh panel lays in contact with the essentially flat backside of the breast implant, the second mesh panel lays in contact with the convex frontside of the breast implant, and the first and second arms extend across opposite lateral surfaces of the breast implant and through the respective first and second openings.

2. The breast implant assembly according to claim 1, wherein:
- the first arm has a length $L_1$, wherein 70 mm$\leq L_1 \leq$180 mm, and
- the second arm has a length $L_2$, wherein 70 mm$\leq L_2 \leq$180 mm.

3. The mesh support device breast implant assembly according to claim 1, wherein;
- the first arm has a length $L_1$, wherein 110 mm$\leq L_1 \leq$150 mm, and
- the second arm has a length $L_2$, wherein 110 mm$\leq L_2 \leq$150 mm.

4. The breast implant assembly according to claim 1, wherein:
- the first mesh panel comprises:
  - a third arm located at the first side of the first mesh panel, and
  - a fourth arm located at the second side of the first mesh panel; and
- the second mesh panel comprises:
  - a third opening configured to receive the third arm, and
  - a fourth opening configured to receive the fourth arm.

5. The breast implant assembly according to claim 1, wherein each opening has an inner perimeter or configuration with at least one dimension that is smaller than a corresponding dimension of the arm that is arranged to be inserted therethrough, such that a friction locking is created once the arm has been inserted through the respective opening.

6. The breast implant assembly according to claim 1, wherein the first mesh panel is made from a first material and the second mesh panel is made from a second material, the second material being different from the first material.

7. The breast implant assembly according to claim 6, wherein the first and second materials are bio-degradable materials having different degradation times.

8. The breast implant assembly according to claim 1, wherein the first mesh panel and the second mesh panel are cut out from the same piece of mesh material.

9. The breast implant assembly according to claim 8, wherein the first and second arms are panels that have been cut out from the same piece of mesh material.

10. The breast implant assembly according to claim 8, wherein the mesh material is a bio-degradable mesh material.

11. The breast implant assembly according to claim 1, wherein an outer end of the first arm and/or an outer end of the second arm is pointed.

12. The breast implant assembly according to claim 1, wherein an outer end of the first arm and/or an outer end of the second arm comprises a stiffener.

13. The breast implant assembly according to claim 1, wherein an edge of the first arm and an edge of the second arm are colinear with an edge of the first mesh panel on a side opposite the second mesh panel.

14. The breast implant assembly according to claim 1, wherein:

the first arm has a length $L_1$, wherein 30 mm≤$L_1$≤210 mm, and the second arm has a length $L_2$, wherein 30 mm≤$L_2$≤210 mm.

15. The breast implant assembly according to claim 1, wherein:

an upper portion of the essentially flat backside of the breast implant is exposed from the mesh support device.

16. The breast implant assembly according to claim 1, wherein:

the first and second arms extend across an upper half of the breast implant.

17. A breast implant assembly comprising:

a breast implant having a convex frontside and an essentially flat backside; and a mesh support device comprising:

a first mesh panel comprising:

a first arm located at a first side of the first mesh panel, and a second arm located at a second side of the first mesh panel opposite the first side, wherein:

the first arm and the second arm extend from the first mesh panel in substantially opposite directions; and a second mesh panel connected to the first panel, the second mesh panel comprising:

a first opening configured to receive the first arm, and a second opening configured to receive the second arm; wherein:

the first mesh panel and the second mesh panel are connected at a waist having a width less than a width of the first mesh panel and a width of the second mesh panel; and an area and/or the width of the second mesh panel is less than an area and/or the width of the first mesh panel; wherein:

the waist is located at a bottom of the breast implant, and the support device is folded at the waist such that the second mesh panel lays in contact with the essentially flat backside of the breast implant, the first mesh panel lays in contact with the convex frontside of the breast implant, and the first and second arms extend across opposite lateral surfaces of the breast implant and through the respective first and second openings.

18. The breast implant assembly according to claim 17, wherein:

the first arm has a length $L_1$, wherein 30 mm≤$L_1$≤210 mm, and the second arm has a length $L_2$, wherein 30 mm≤$L_2$≤210 mm.

19. The breast implant assembly according to claim 17, wherein:

an upper portion of the essentially flat backside of the breast implant is exposed from the mesh support device.

20. The breast implant assembly according to claim 17, wherein:

the first and second arms extend across an upper half of the breast implant.

* * * * *